United States Patent
Latorre et al.

(10) Patent No.: US 11,636,776 B2
(45) Date of Patent: Apr. 25, 2023

(54) UNIFIED IDENTIFICATION PROTOCOL IN TRAINING AND HEALTH

(71) Applicant: CONÉCTATE SOLUCIONES Y APLICACIONES SL, Soria (ES)

(72) Inventors: Fernando Latorre, Soria (ES); Nuria Sala, Soria (ES)

(73) Assignee: CONÉCTATE SOLUCIONES Y APLICACIONES SL, Soria (ES)

( * ) Notice: Subject to any disclaimer, the term of this patent is extended or adjusted under 35 U.S.C. 154(b) by 847 days.

(21) Appl. No.: 16/452,598

(22) Filed: Jun. 26, 2019

(65) Prior Publication Data
US 2020/0211409 A1    Jul. 2, 2020

(30) Foreign Application Priority Data
Dec. 28, 2018   (ES) .............................. ES201832006U (51) Int. Cl.
*G09B 19/00* (2006.01)
*G16H 20/30* (2018.01)
*H04L 9/08* (2006.01)
*H04L 9/32* (2006.01)

(52) U.S. Cl.
CPC ............. *G09B 19/00* (2013.01); *G16H 20/30* (2018.01); *H04L 9/0861* (2013.01); *H04L 9/3242* (2013.01)

(58) Field of Classification Search
CPC .. G09B 19/00; H04L 9/32; H04L 9/08; G16H 20/30
USPC ........................................... 709/827; 707/827
See application file for complete search history.

(56) References Cited

U.S. PATENT DOCUMENTS

2013/0096943 A1* 4/2013 Carey ................. G06F 21/6263
                                                                    705/2
2015/0143468 A1* 5/2015 Hebert .................... H04L 63/06
                                                                    726/4

\* cited by examiner

*Primary Examiner* — Sibte H Bukhari
(74) *Attorney, Agent, or Firm* — Norton Rose Fulbright Canada LLP; Maya Medeiros (57) ABSTRACT

The present invention discloses a unified identification protocol for training and health, comprising: unified multipurpose identifier that serves to identify individuals and the relationships established with these individuals, such as relationships with entities, professionals, products, services and transactions, generation of a multipurpose identifier, unique, non-transferable and univocally distinguishable through a computer system. The computer system that identifies them universally to avoid identification errors, based on UUID, DID and/or other formats and unify the data of the same individual existing in different systems, stored in one or several electronic devices of the individual and/or their legal guardians and, additionally, in one or more cloud services, certify access permissions granted/revoked to the different data compartments in the profile of the individual and the authenticity of the data, carried out in one or more distributed data ledger technologies or blockchains.

19 Claims, 1 Drawing Sheet

UNIFIED IDENTIFICATION PROTOCOL IN TRAINING AND HEALTH

TECHNICAL FIELD

The invention is generally directed to health and training sectors, encompassing at the same time, identity and data management systems. More particularly the invention relates to a unified identification protocol in training and health.

BACKGROUND OF THE INVENTION

Training can be defined as the action of teaching, to a person or animal, a particular skill to do a job or activity, or type of behavior. Training is teaching, or developing in oneself or others, any skills and knowledge that relate to specific useful competencies. Training has specific goals: improving capability, capacity, productivity and performance.

In some countries (India, United Kingdom, Australia, Singapore, . . . ) as well as in some regions (such as in Canada), a course is the entire programme of studies required to complete a university degree, and the word "unit" or "module" would be used to refer to an academic course as it is referred to in other parts of the world, for example North America and the rest of Europe.

In higher education in some countries (Canada, United States, . . . ) a course is a unit of teaching that typically lasts one academic term, is led by one or more instructors (teachers or professors); a course is usually an individual subject and students may receive a grade and academic credit after completion of the course.

Courses are time-limited in most cases. There are professional courses, health and social care courses, etc. In the health area, the Joint Committee on Health Education and Promotion Terminology of 2001 defined Health Education as "any combination of planned learning experiences based on sound theories that provide individuals, groups, and communities the opportunity to acquire information and the skills needed to make quality health decisions." The World Health Organization defined Health Education as "comprising of consciously constructed opportunities for learning involving some form of communication designed to improve health literacy, including improving knowledge, and developing life skills which are conducive to individual and community health."

Additionally, Patient Education is defined by the American Academy of Family Physicians as "process that changes or enhances a patient's knowledge, attitude or skills to maintain or improve health". As is well known, the information regarding health education and health courses for self-care education of patients, caregivers and family members, as well as for any other user, can be very extensive and varied, from those for the chronically ill, diabetic, hypertensive, etc., to courses aimed at healthy population with clear interest in increasing their knowledge in health, healthy living, improvements in their daily living habits, etc., to achieve the empowerment of users within the health system.

The information regarding health courses for self-care education of patients, caregivers and family members, as well as for any other user, can be very extensive and varied, from those for the chronically ill, diabetic, hypertensive, etc., to courses aimed at healthy population with clear interest in increasing their knowledge in health, healthy living, improvements in their daily living habits, etc., to achieve the empowerment of users within the health system.

Health education offered for self-care in health centers and health educational training centers is provided by health professionals who train patients, caregivers and other users to modify health behaviors and improve health status. It serves as a prevention and/or health promotional tool and also as a training tool and specific information for certain diseases, both for patients and for family members, caregivers and other users.

The results obtained with the health education provided in self-care education programs are a greater involvement and better monitoring of health, treatments and diseases, reduce the number of medical visits and a greater degree of knowledge to decide freely about the disease and/or treatment. The programs and/or courses of the self-care education programs and health training centers for self-care management education help people to gain self-confidence in their ability to control their symptoms and control how their health problems affect their lives. They are effective tools to help people with chronic diseases.

However, until now there is no common and centralized system for obtaining information related to courses by people interested in professional training, health training and other training areas, nor is there a common and centralized system to record courses conducted by the same individual and/or acquired training, with which, although some of them have attended a previous course, the public/private entities have no possibility of knowing which people may be interested in the courses they offer to extend or complete the education, training and/or competence of users, so that each entity must get and collect data from potential individuals to offer their training courses independently and in isolation.

It must be noted that the Health Insurance Portability and Accountability Act of 1996 (HIPAA) outlines a process to achieve uniform health data standards and health information privacy in the United States. Among these standards are: certain uniform transactions and data elements for health claims and equivalent encounter information, claims attachments, health care payment and remittance advice, health plan enrollment and disenrollment, health plan eligibility, health plan premium payments, first report of injury, health claim status, referral certification and authorization, and for coordination of benefits. Unique identifiers for individuals, employers, health plans, and health care providers for use in the health care system. Code sets and classification systems are designed for the data elements of the transactions identified and security standards for health information. Moreover, standards for procedures for the electronic transmission and authentication of signatures with respect to the transactions identified. Privacy and confidentiality protections for health information play a prominent role in the law as well.

In other hand, as more people use the internet and/or medical chatbots to understand their health issues, some also go online to buy prescription medication. But many online pharmacies are unregistered and it can be difficult to distinguish between registered online pharmacies and other commercial websites, so buying from them is potentially unsafe. Medication from an unregistered website could also be dangerous because it might be out-of-date, diluted or fake. For prescription-only medicines, an online pharmacy must receive a legally valid prescription before dispensing the medication.

Medication, such as Viagra for erectile dysfunction, and the cholesterol-lowering medication Lipitor (Atorvastatin), are often sold cheaply online and without a practitioner prescription or the advice of a pharmacist. This is risky because medication should only be taken under the supervision of a healthcare professional. Their guidance on whether a medication is suitable for the individual, the dosage, possible side effects, and any harmful interactions with other medications is crucial. Moreover, fake practitioners put the public at risk, and is needed a unified and universal certification of health professionals in every territory which protects the public, ensuring properly qualified and educated practitioners (nurse, midwife, doctor, psychologist, dentist, . . . ) and to enable the public to check and ensure they are consulting with a registered and certified health practitioner.

Health tourism is a wider term for travel that focuses on medical treatments and the use of healthcare services. It covers a wide field of health-oriented, tourism ranging from preventive and health-conductive treatment to rehabilitation and curative forms of travel. Wellness tourism is a related field. Medical tourism refers to people traveling to a country other than their own to obtain medical treatment and most often is for surgeries (cosmetic or otherwise) or similar treatments, though people also travel for dental tourism or fertility tourism. People with rare conditions may travel to countries where the treatment is better understood. However, almost all types of health care are available, including psychiatry, alternative medicine, convalescent care, and even burial services.

Currently there is no universal system to identify the same individual in any organization and territory. For example, patent U.S. Pat. No. 4,707,592 defined a personal universal identity card system for failsafe interactive financial transactions, but it is only for persons and had not defined the way to incorporate information such as professional and/or health competences. U.S. Pat. No. 10,032,166 relies on a centralized identity authentication for electronic communication networks which include a personal identification number and a dynamically changing non-predictable code, but not a usable universal identifier for individuals. Neither does the U.S. Pat. No. 8,522,358 for a "Universal identity service avatar ecosystem", related to collecting user information and forming one or more avatars that are based on the user's collected information, defines a usable universal identifier for individuals.

There are numerous national eID programs initiated (including card and/or mobile-based schemes). Examples include the European Union's Electronic Identification and Signature (eIDAS), Canada, Australia, Algeria, Cameroon, Ecuador, Jordan, Iran, Japan, Senegal, Thailand, etc. The US Commerce Department's National Institute of Standards and Technology (NIST) awarded a federal grant to further support development of trusted identities, based on the Digital driver's license. Some of these programs now include biometrics, the majority in the form of fingerprints.

Also, early tests of blockchain technologies took place in Estonia and in the UK, other projects use Decentralized Identifiers (DID) such as Sovrin and Solid. Additionally, other initiatives exist such as Civic, ID2020 for refugees, and blockchain wallets such as Pillar project, SelfKey and others. But currently usable unified cross-border universal identifiers for individuals doesn't exist.

Object identifiers or OIDs are an identifier mechanism standardized by the International Telecommunications Union (ITU) and ISO/IEC for naming any object, concept, or "thing" with a globally unambiguous persistent name. OIDs are paths in a tree structure, with the left-most number representing the root and the right-most number representing a leaf. Each OID is created by a Registration Authority. Each of these authorities may, in turn, delegate assignment of new OIDs under it to other registration authorities that work under its auspices, and so on down the line. Eventually, one of these authorities assigns a unique (to it) number that corresponds to a leaf node on the tree. The leaf may represent a registration authority (in which case the OID identifies the authority), or an instance of an object. A registration authority owns the namespace consisting of its sub-tree. OIDs can be allocated by any organization using a unique OID root. IANA assigns Private Enterprise Numbers (PEN) to companies and other organizations under the 1.3.6.1.4.1 node. OIDs down-tree from these is among the most commonly seen. Health Level Seven (HL7), a standards-developing organization in the area of electronic health care data exchange maintains its own OID registry. DICOM uses OIDs and, also, the Centers for Disease Control and Prevention uses OIDs to manage the many complex values sets or "vocabularies" used in the Public Health Information Network (PHIN) Vocabulary Access and Distribution System (VADS).

A single message can use OIDs from various sources and a single scheme can be identified by more than one OID (e.g. by an OID from more than one organization). Once issued, an OID is never withdrawn and always identifies the same scheme or object. For example, 1.3.6.1.4.1.19126.3 refers to the National Identity Document in Spain (DNI), the OID number 2.16.724.4.30 refers to the Registered Physician Number in Spain (College of Physicians), the OID number 2.16.724.4.303 refers to the Registered Pharmacist Number in Spain (College of Pharmacists), and also there are OID numbers for each Spanish region.

In other hand, a UUID (Universal Unique Identifier) is a 128-bit number used to uniquely identify some object or entity on the Internet. A UUID is an identifier that is unique across both space and time, with respect to the space of all UUIDs, by using cryptographic-quality random numbers. UUIDs are standardized by the Open Software Foundation (OSF) as part of the Distributed Computing Environment (DCE).

The UUID relies upon a combination of components to ensure uniqueness. In its canonical textual representation, the 16 octets of a UUID are represented as 32 hexadecimal (base-16) digits, displayed in 5 groups separated by hyphens, in the form 8-4-4-4-12 for a total of 36 characters (32 alphanumeric characters and 4 hyphens). In an UUID example xxxxxxxx-xxxx-Mxxx-Nxxx-xxxxxxxxxxxx the 4 bits of digit M indicate the UUID version, and the 1-3 most significant bits of digit N indicate the UUID variant. UUID Version 4 is randomly generated and M indicates version 4. Version-5 UUIDs are generated by hashing a namespace identifier and name (uses SHA-1) and the namespace identifier is itself a UUID. The specification provides UUIDs to represent the namespaces for URLs, fully qualified domain names, object identifiers, and X.500 distinguished names; but any desired UUID may be used as a namespace designator. Version-5 UUIDs have the property that the same namespace and name will map to the same UUID. However, neither the namespace nor name can be determined from the UUID, given the other, except by brute-force search.

Uniform Resource Name namespace (URN) for UUIDs is an Internet standards track unified identification protocol. A UUID can be used for multiple purposes, from tagging objects with an extremely short lifetime, to reliably identifying very persistent objects across a network, particularly (but not necessarily) as part of an ASN.1 object identifier (OID) value, or in a Uniform Resource Name (URN). A URN (IETF RFC 2141) formed using a UUID shall be the string "urn: uuid:" followed by the hexadecimal representation of a UUID. The following is an example of the string representation of a UUID as a URN: urn:uuid:f81d4fae-7dec-11d0-a765-00a0c91e6bf6.

UUIDs forming a component of an OID are represented in ASN.1 value notation as the decimal representation of their integer value, but for all other display purposes it is more usual to represent them with hexadecimal digits with a hyphen separating the different fields within the 16-octet UUID. This representation is defined in Rec. ITU-T X.667|ISO/IEC 9834-8. A UUID can be encoded as an OID very simply. An OID that begins with "2.25." is an OID encoded UUID. The value after "2.25." is the straight decimal encoding of the UUID as an integer. It MUST be a direct decimal encoding of the single integer, all 128 bits. It must not be broken up into parts. E.g., the UUID "f81d4fae-7dec-11d0-a765-00a0c91e6bf6" becomes the OID: "2.25.329800735698586629295641978511506172918".

It must be decimal because OIDs are all decimal. Some unified identification protocols have limits to the size of a Unique ID. For example, DICOM has restricted some OIDs to 64 characters.

There is a URI (URN) encoding for both UUID and OID. For example: urn:oid:2.25.329800735698586629295641978511506172918 urn:uuid:f81d4fae-7dec-11d0-a765-00a0c91e6bf6.

Also, a decentralized identifier (DID) is a new type of globally unique identifier. The specification for DIDs is being created by the World Wide Web Consortium (W3C) and is defined as "a new type of identifier for verifiable, 'self-sovereign' digital identity". It is a scheme with several attributes that uniquely defines a person, object, or organization. Conventional identity management systems are based on centralized authorities, such as corporate directory services or certificate authorities. DIDs are fully under the control of the DID subject, independent from any centralized registry, identity provider, or certificate authority. The emergence of blockchain technology provides the opportunity to implement fully decentralized identity management (DIDM). In DIDM, all identity owners share a common root of trust in the form of a globally distributed ledger. Each DID record is cryptographically secured by private keys under the identity owner's control. It is believed to be the missing link to redefine the security values of the Internet, as it can become the identity layer of the Internet.

DIDs could be adapted to work with multiple blockchains by following the same basic pattern as the URN specification. The key difference is that with DIDs the namespace component identifies a DID method, and a DID method specification specifies the format of the method-specific identifier. All DID method specs must define the format and generation of the method-specific identifier, which must be unique in the namespace of that DID method. DIDs provide a path to service agnostic data portability (e.g. switching between Verifiable Credential digital wallet providers). All types of identifier systems may add support for DIDs. This creates an interoperability bridge between the worlds of centralized, federated, and decentralized identifiers.

A user can create a new DID at any time and for any reason. A DID is two things: a unique identifier and an associated DID Document. The unique identifier looks something like "did: example:123456789abcdefghi" and it's the unique ID for looking up a DID document. A DID Document is a JSON-LD object that is stored in some central location so that it can be easily looked up. The DID is expected to be "persistent and immutable" so that it is outside of the influence of anyone other than it's owner. The result of resolving a DID may be cryptographically signed to ensure its integrity. The resolution also provides one or more public keys associated with the DID. Using cryptographic keys, the owner can prove they are in control of the DID. Parties who have exchanged DIDs can mutually authenticate each other and encrypt their communication.

The DID Document must include a DID. It might include things like: a timestamp of when it was created, a cryptographic proof that the DID Document is valid, a list of cryptographic public keys, a list of ways that the DID can be used to authenticate, a list of services where the DID can be used any number of externally defined extensions.

The DID Document is the root record for a decentralized identifier that can reference not only what's in the DID Document itself, but also any information from the service endpoints. This is accomplished by adding selectors, paths, query parameters, and fragments to the DID. The selector is used to identify a particular part of the DID Document. If the DID also includes a path, that is appended to the URL given in the service's "serviceEndpoint" attribute before the endpoint is called. For example, the following DID: did:example:123456789abcdefghij;exam_svc/foo/bar?a=1#flip is equivalent to the following URL: https://example.com/endpoint/8377464/foo/bar?a=1#flip.

Through this mechanism, DIDs provide a permanent, resolvable identifier for any Internet service. For example, If one of the service endpoints in the DID Document is for email, the user can change the email address at will and anyone holding that DID will still be able to reach the user's email. DIDs represent a universal addressing, abstraction, and verification layer for key pairs, endpoints, and any other information we wish to include in the DID Document. Layer verifiable credential exchange on top of this for multi-source identity and this constitutes a significant upgrade to online identity.

A universal identity system must support both "omnidirectional" identifiers for use by public entities and "unidirectional" identifiers for use by private entities, thus facilitating discovery while preventing unnecessary release of correlation handles. The availability of private DIDs has significant advantages, exchanged between parties to a relationship and resolvable only within that relationship. Practically speaking, private DIDs allow for greater scalability of the DID resolution infrastructure. Private DIDs reduce access to correlatable identifiers by third parties increasing privacy protections.

However, the EU General Data Protection Regulation (GDPR) puts some limitations in the utilization of blockchain for identity purposes. This regulation is designed to strengthen privacy and personal data protection in the EU, by giving private persons more control over their personal data and explicitly includes "online identifier[s]". Under the GDPR, personal data even includes data that has undergone "pseudonymization," meaning that the data has been processed such that it "can no longer be attributed to a specific data subject without the use of additional information". It is well-established that data that has been encrypted or hashed is not irreversibly anonymised. Pseudonymous data, unlike anonymous data, still allows for re-identification. Pseudonymization techniques make it more challenging for users to identify data subjects, but it does not "scrub" all identifying personal information. Blockchain and GDPR main point of conflict is the right to be forgotten. The immutable nature of the blockchain's decentralized ledger is a core idea within blockchain technology and ensures the absolute integrity of the records in the chain in terms of security and accuracy. Due to the blockchain "immutability of records" principle, any data contained on the blockchain transactions are virtually impossible to modify or being erased to meet GDPR requirements.

The application US-2018-0247346-A1, which in turn is a continuation of the patent PCT/ES2016/070428 and which in turn is a continuation of the patent in Spain P201531611, now allows a unified global registry of blood donors and other types to be available through the unification of different health cards for the same individual and a universal identification of individuals (donors). It also allows knowledge of other relevant health data related with the individual, which makes it possible to improve the safety and to know the health history of an individual and thus improve the safety and the attention to the individual in different public or private organizations and in different territories.

The procedure for unified global registry and universal identification of products of biological origin for medicinal purposes (U.S. Pat. No. 16,169,126) utilizes and expands the use of the universal donor identifier. Said procedure allows generating, global public and private identifiers, unique and non-transferable, as well as the unique identification codes of: products of biological origin, individuals (as donors, clients, users and patients, both human or animal), cellular production lines, entities (such as companies, organizations, donation centers, medical centers, clinics, hospitals, laboratories), related personnel and devices to access the system and clinical interventions.

As described in the U.S. Pat. No. 16,169,126 application, product identification code contains product identifiers from one or more countries, one or more product labeling systems and, additionally, one or more links to web addresses. The procedure generates: a global data vault for each part, one or several data vaults associated with the global vault (compliance with local data storage laws), one or several data profiles associated with each vault for each part; a unique public identifier associated with the global data vault; a unique private identifier associated with the global data vault.

The object of the proposed invention is to improve health and attention to individuals through their empowerment, developed through a unified and universal multipurpose identifier and the certification of the steps and processes carried out through the identifiers generated for the individual and for the entities, services and processes, so that the different parties can use them in a fast and practical way.

From the point of view that every individual is a potential donor from the moment of birth, it makes sense to preferably associate the existing universal donor identifier as the universal health identifier associated with each individual to identify it univocally from the moment of birth, and also use it as a universal identifier associated for each individual which can be associated with their biological parents or legal guardians and with different public/private identifiers (legal identity identifiers and distinct identifiers from different public/private organizations).

As novelty, this unified identification protocol defines the way to unify the data of the same individual from different sources and to universally identify individuals and products, services, processes and transactions from different entities trough a unified multipurpose identifier, including the way to unify certification of professionals in every territory, ensuring properly qualified and educated practitioners (nurse, midwife, doctor, psychologist, dentist, . . . ) and to enable the public to check and ensure they are consulting with a registered professional such as certified training professionals and registered practitioners.

The proposed invention combines above mentioned technologies and standards with the aim of avoid the drawbacks noted above. Through its correct implementation it is possible to empower individuals to be the owners of their own data in a unified manner and this data is available in any territory and for any relationship established with and authorized by the individuals themselves or by their legal guardians, and for the verification of the authenticity of each data. It allows individuals to share their data with entities and/or professionals and manage it on their own terms. By using decentralized blockchain principle with identity verification, and adding a unified and universal multipurpose identifier for different uses such as an identifier for individuals (users, trainers, health professionals, among others) and for each relationship established with the individual such as relationships with other individuals (e.g. legal guardians), entities (private relationships with each entity such as client, employee, provider, . . . ), products and services (health and training services, devices and medications, health and training programs . . . ) and transactions (enrollments, prescriptions, payments, competence levels obtained, data exchanges, granting/revoking access rights, . . . ), the proposed unified identification protocol acts as a unified and universal verifiable digital watermark which can be assigned to them and helps the different parties to check and verify the identity and the data authenticity in real time, hence, eliminating rate of fraud.

An example of use of what this invention allows is described below: Thanks to the existence of the proposed unified identification protocol for the unified identification in health and training, a person with a stress problem can find qualified registered physicians, verify their qualification and competences and make an appointment. In the medical consultation, the individual is identified through the unified multipurpose identifier in the mobile phone (through an installed app) and a private relationship identifier is generated to securely exchange the data information with the physician. If the digital identity of the individual hasn't been officially verified, the physician can act as verifier and do the verification after probing the individual's identity with some official document, which will be certified in the blockchain. Hypertension is detected in the individual in the consultation and drugs such as sedatives and high blood pressure medications are prescribed. The individual makes the payment to the physician through the multipurpose identifier and thanks to a payment mode configured by the user. Automatically both the physician receives the payment and the individual receives the prescription as well as the medical report in the users' mobile phone, both certified in the blockchain. After that, the user can find trough the unified identification protocol registered pharmacies and then the user selects a pharmacy to send the prescription for making the purchase. The pharmacy checks the authenticity of the prescription, sell the medicines to the individual and the transaction is certified in the blockchain. Subsequently, the individual decides to hire a trip to treat their stress problem, in a different country. The package includes flight, private transportation, hotel accommodation, spa treatment, medical supervision and care by a specialized psychologist. Thanks to this unified identification protocol the individual can check the authenticity of the trip agency, flight company, hotel, the qualification of the physician and psychologist and also verify their registrations and licenses. The individual is identified in the consultation trough the multipurpose identifier and the physician get access to the medical data of the user after the user approves that. During the medical examination in the contracted package, a cardiac arrhythmia is detected in the individual and medication is prescribed. In addition, the individual decides to participate in a patient empowerment program for self-care and share their anonymous data for research. Data is sent to the user, certified in blockchain and, additionally, anonymised and stored in a FHIR cloud system for research purposes. After that, both physicians and psychologist can make monitor the health status of the individual and their progression in self-care and healthy life.

As the world becomes more digitally driven, it only seems logical to document transactions with a more convenient, secure method to eliminate human error. A blockchain-certified unified identification protocol creates greater trust for all parties, enables added compliance and transparency in the system, makes for better digital tracking and identifies fraud more easily, for example, to identify and offer services such as patient education courses by certified registered entities and professionals, to recruit and/or recover either new users or individuals from other courses, empowering self-care education, whether an individual is associated with a health or training center in one or more territories or if there is no previous participation.

Finally, in reference to the current state of the art, it should be noted that, although are known distinct identifiers and identity systems exists in the market, at least on the part of the applicant, the existence of any unified identification protocol with technical and constitutive characteristics similar to those presented by the invention that is asserted here is unknown.

SUMMARY OF THE INVENTION

The invention, as expressed in the statement of this descriptive report, refers to a unified identification protocol whose purpose is to facilitate the identification of individuals, entities, processes and transactions carried out, in a unified manner in one or more territories, through a set of steps, to empower the individual and achieve the unification of their identifiers and their data in different systems, promote their health training, as well as improve the attention to the individual and their safety.

The object of the invention is to improve health and attention to individuals through their empowerment, developed through a unified and universal multipurpose identifier and the certification of the steps and processes carried out through the identifiers generated for the individual and for the entities, services and processes, so that the different parties can use them in a fast and practical way, such as, but not limited to, health training centers, and that can be used, as a non-limiting example, to offer courses and recruit/recover users in health or training centers, in one or more territories, whether a person is associated with a health or training center or if there is no prior participation.

The disclosed unified identification protocol utilizes a unified multipurpose identifier that serves to identify individuals (both humans and animals) and the relationships established with these individuals, such as relationships with entities (health and training centers, among others), professionals, products and services (such as health and training procedures, self-care education programs, use of devices and medications, . . . ) and transactions (enrollments, competence levels, data exchanges, identity verifications, granting/revoking access rights, . . . ), said unified identification protocol consisting in a series of steps such as: generate a multipurpose identifier code, unique, non-transferable and univocally distinguishable for each of them (individual, entity, service or product, transaction, . . . ) through a computer system, that identifies them universally to avoid identification errors, based on UUID, DID and/or other formats; unify the data of the same individual existing in different systems, stored in one or several electronic devices of the individual and/or their legal guardians and, additionally, in one or more cloud services (backup copies, data for emergencies, . . . ); manage and certify access permissions granted/revoked to the different data compartments in the profile of the individual (different health areas, as well as different entities, services and devices associated with the individual); certify the authenticity of all previous data, carried out in one or more distributed data ledger technologies or blockchains.

The data of the individual is securely encrypted and locally stored in one or more electronic devices of one or more users (the individual and other legal guardians) such as mobile phones, smart watches, tablets and/or computers, and is managed by the user or by one or more verified legal guardians (registered and associated with such individual in the system).

The identifiers and other required data are stored and certified as a digital record in cloud system(s) and in one or more distributed ledger technologies or blockchains to which individuals, entities and different systems can access.

In a preferred embodiment of the invention, the unified identification protocol creates multipurpose identifiers, unique, non-transferable and univocally distinguishable such as individual identifiers, personal identifiers, health Identifiers, identity identifiers, entity identifiers, listing identifiers for professional services, relationship identifiers, client Identifiers, executed transaction identifiers, training course identifiers, process/product identifiers, qualification identifiers, biometric identifiers, wallet identifiers, device identifiers, among others, by means of a set of alphanumeric characters defined by alphanumeric-hexadecimal translation maps that avoid confusion among them by a bad reading, based both on UUID, OID, DID formats and others, codified in QR, NFC, and other formats including additional information, and which are available for automatic reading by electronic devices (MRI) and for human reading (HRI).

In a preferred embodiment of the invention, the unified identification protocol creates multipurpose identifiers, unique, non-transferable and univocally distinguishable for the relationships established between individuals and other individuals (such as professionals), entities, processes, products and services, devices and for other information transactions, and different types of information can be contained and exchanged between them, such as unencrypted, encrypted and/or anonymised, that information can be certified as true and legitimate by registered, certified and authorized entities, professionals and employees and can be verified by the different parties.

In a preferred embodiment of the invention, the identification of the individual is the sum of the individual's multipurpose identifier deposited in the electronic device (mobile, tablet, . . . ) and/or in a microchip implant plus one or several biometric signals associated with the individual's multipurpose identifier (fingerprint, retina, . . . ).

In a preferred embodiment of the invention, the data communication is performed on a common medium safe for the data exchange and data storage and the information is exchanged in custom fields, in a unified manner among the different systems, formats, and standards available (vCard, FHIR, LOINC forms, MSON, HTTP headers, JWTs, JSON, . . . ) by using for the field name the character "X"

followed by a hyphen and then the characters "UHC" or similar, and then another hyphen followed by the name of the field.

In a preferred embodiment of the invention, the information can be exchanged off-line in situations or locations with little mobile network and/or WiFi connectivity or when the connection is not available (e.g., natural disasters), using NFC, Bluetooth, ad hoc mobile network (MANET) and even visual codes for data transmission (such as QR codes), by means of maintaining a memory cache both the application of the individual and the organization and/ or staff requesting access to information, these memory caches containing both information of organizations, people and devices to which they have authorized access to the data and also information received from the system to be able to validate the authenticity of the other party in off-line mode.

In a preferred embodiment of the invention, the individuals' profiles, the different compartments and the data objects contained can be securely backed up, splitted and replicated in one or several online services and/or in one or more electronic devices of the user or of some selected contacts, so that backup can be combined and the data recovered from these splitted, distributed and replicated encrypted backup copies, in case of data loss and/or broken device.

In a preferred embodiment of the invention, wearable devices, health/sports devices and other sensors or devices can be associated to the individual's profile, creation of a relationship for each one, associate access rights for that relationship, storage the device data in the electronic device of the individual and/or in the cloud system(s), associate access rights both to each specific device and to the data related, automatic update of the individual's profile and automatic data exchange with the different relationships if approved by the user.

In a preferred embodiment of the invention, the application of the individual or a device may issue the geolocation of the individual and, optionally, publish this information in the system, either anonymously or non-anonymously for certain contacts, organizations or personnel, in such a way that any individual can detect the presence of other (s) within a certain radius of action and the application of the individual or a device may detect a problem, emergency or accident automatically or manually by a specific button in the application or on the device, and the unified identification protocol can send information to the emergency services and/or designated emergency contacts, by SMS or other embodiments, including the individual multipurpose identifier, device (s) multipurpose identifier (s), application and/or device's data, geolocation of the individual or the last known (s), WiFi or other detected nearby networks, as well as information for emergencies approved by the individual, among others.

In a preferred embodiment of the invention, the unified identification protocol allows to have different payments modes associated with an individual, entity and/or established relationships, and the multipurpose identifier can be used to make payments manually and/or automatically (such as smart-contracts).

In a preferred embodiment of the invention, authorized personnel can monitor the data shared from the individual's multipurpose identifier through the established relationship by the different data compartments and devices associated with the individual's multipurpose identifier and approved in the relationship's access rights, so that the authorized personnel can view past data and real time data from the different devices and can make suggestions or diagnoses to improve the health of the individual.

In a preferred embodiment of the invention, the individual(s) or their legal guardian(s) can establish a relationship to share certain data for research purposes from their multipurpose identifier, associated to individual's profile(s) and devices, through anonymised data exchange.

In a preferred embodiment of the invention, there are different types of data for sharing: public, private, emergencies and anonymised data. Public and anonymised data can be shared without encryption, for example by NFC or QR code through vCard standard format, and also health data can be shared trough FHIR standard. Private and emergencies data are cypher texts. Emergencies data encryption is managed by the system and the system will provide the data approved by the user for this case to certified emergency services. Private data encryption is self-managed by the user. Some required data by an entity can be sent from the servers of the cloud system(s) accessible by the different parties if the user has previously given authorization for permanent access to said data, for example data for emergencies.

In a preferred embodiment of the invention, the private data is encrypted in the user mobile and the user can share this data generating a re-encryption key, using asymmetric key encryption. The re-encryption key is generated by the user using the public keys provided by the approved recipients, and this re-encryption key is used to re-encrypt the cypher text of the user, which is transmitted and decrypted by each of the approved recipients through their own private key.

In a preferred embodiment of the invention, user can approve some recipients to automatically access some data without continuously asking for the user approbation. The system translates cypher texts encrypted under user key into cypher texts encrypted under the recipients' keys. The system acts a re-encryption proxy and it never see the content of the messages being translated, nor can it re-encrypt user's messages to users for whom the user has not granted decryption rights.

In a preferred embodiment of the invention, when a package of services or products are contracted by the users, they can verify the authenticity of the whole pack and of all of its parts, such as verifying the authenticity of drugs and of the registered pharmacy when buying prescribed medication, as well as verifying the authenticity of a medical tourism pack and its components such as the agency, flight, hotel, medical center, registered practitioner(s), professional qualification and products/devices being used in the procedure, among others.

In a preferred embodiment of the invention, the product or device identifier is associated with one or more identifiers of the product/device and/or of some of its parts, such as: chemical composition and/or cellular production line identification; processor, memory, and/or network card identification; among others.

In a preferred embodiment of the invention, a specific object in the proposed unified identification protocol (individual, organization, service, device, product, etc.) can be associated with or can create one or more distinct multipurpose identifiers for verification of different information, such as verifiable information as client (date of birth, sex, personal contact data . . . ), verifiable information in emergencies (name, nationality, medical data, . . . ), verifiable claims for data as provider (quality certification, qualification certification, business data, . . . ) or legal and administrative verifiable information (e.g. date and registration number in the Chamber of Commerce, civil registry, tax registry), among others.

In a preferred embodiment of the invention, a user, professional, service and/ or organization can receive recognitions and/or rewards (diploma, real or virtual award, virtual currency or digital money, fungible or non-fungible tokens . . . ) after reaching some goal (training or qualification acquired, services performed, degree of quality achieved, . . . ). Additionally, the recognitions and/or rewards obtained can be used to achieve new objectives (to carry out new training/programs, enable access to higher level, etc.).

The unified identification protocol allows to share data from different sources related to the same individual, to have the data unified in the individual's profile in a universal manner, to verify the authenticity of the information related to a same individual and also to know the authenticity of registered professionals and their qualification (such as in health, training and other areas.)

BRIEF DESCRIPTION OF THE DRAWINGS

The embodiments herein will be better understood from the following detailed description with reference to the drawings, in which.

DETAILED DESCRIPTION OF THE INVENTION

The unified identification unified identification protocol in training and health that the invention proposes, is configured, therefore, as a novelty within its field of application, since according to its implementation the objectives outlined above are satisfactorily achieved, their characterizing details conveniently collected in the final claims accompanying the present specification.

Figure 1:
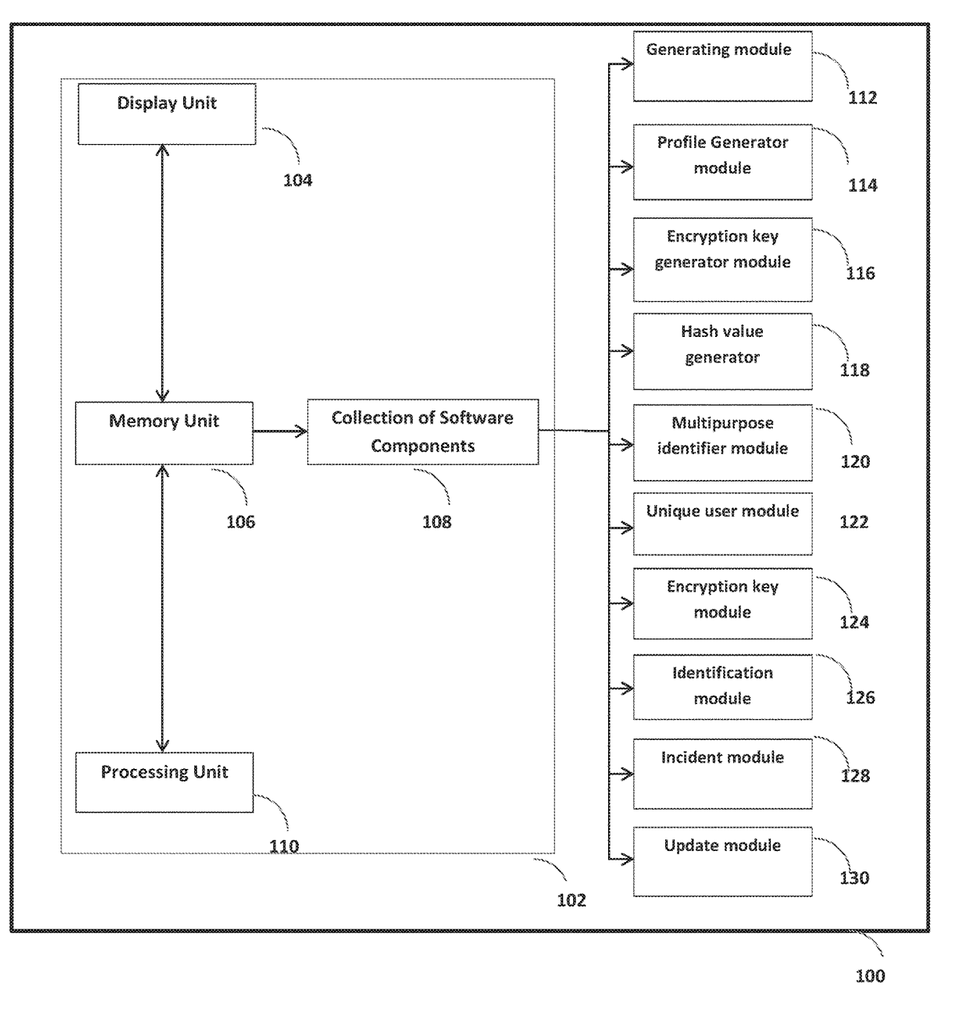
FIG. 1 illustrates an exemplary system to unify and certify a data and an identifier using unified identification protocol in at least two operational phase.

FIG. 1 illustrates a computer implemented system (100) to unify and certify a data and an identifier using a unified identification protocol in at least two operational phases. The computer implemented system (100) comprising: an online electronic device (102), the online network device (102) comprises a display unit (104); a computer processor for processing a collection of software components; and the collection of software components (108) stored in a computer-readable memory unit (106) on a single platform comprises: a generating module (112) configured to generate a group of multipurpose identifiers; a profile generator module (114) configured to generate a unique profile; an encryption key generator module (116) designed to generate at least one or more encryption keys; a hash value generator (118) configured for generating a hash value; a multipurpose identifier module (120) configured to identify a unique profile for each individual and associating with a group of identifiers; a unique user profile module (122) designed to create a unique user profile associated to at least one personal identifiers in one or several user devices; an encryption key module (124) configured for generating at least one encryption key to each of the individual and to different relationship and set of multipurpose identifiers; an identification module (126) designed to identify the unique profile encoded in QR, NFC or other realizations carried out by an entity, a service or an authorized personnel through a software application and to request for accessing an information associated with the group of identifiers for creation of relationship with the encryption keys after receiving a request approval, if no previous relationship and access rights were established between the different parties; an incident module (128) configured to generate, register and automatic communication of an incident in case of existence of any impediment when making the identification, creating the relationship, accessing the data, making requests or exchanging data, and notify to the related multipurpose identifiers; an update module (130) configured to store and updates the information associated with the group of identifiers in a cloud systems, in one or several portable electronic devices of the individual and/or of the legal guardian(s) and in a distributed ledger technology accessible by a set of different parties based on the access permissions obtained and then notify to the related identifiers for making a group of required actions and registering a transaction.

Specifically, what the invention proposes, as indicated above, is a unified identification protocol to unify and certify data and identifiers, in a universal manner in one or more territories, of individuals such as users, trainers and health professionals, among others, and for each relationship established between the individual and: other individuals such as legal guardians; entities such as public administrations, health centers, training centers, insurers, among others; products and services, such as health and training services and programs, medical and/or veterinary procedures for improving health or user monitoring, health training courses for self-care, experimental programs in patient devices used with/by the individual, medications prescribed/used by the individual, among others; transactions, such as enrollments, prescriptions, payments, competence levels obtained, data exchanges, granting/ revoking access rights, among others.

In this way, the unified identification protocol allows to verify the authenticity of both data and processes through certification, in one or more distributed ledger technologies or blockchains, of information about: verified individual's identities (both people and animals), carried out by authorized personnel; processes such as grant/revoke privileges and roles, health training programs, medical and veterinary procedures; qualifications, completion of training programs, virtual awards obtained, competence level obtained; transactions, such as enrollments, payments, rewards, among others.

Every individual (client, professional . . . ), entity, service, product, device (among others) registered in the system will have a unique and universal multipurpose identifier associated to, in a UUID format and/or others. Each of one can have one or more identifiers associated to the multipurpose identifier. Additionally, individuals can have associated distinct public/private identifiers from different entities (legal, academic, work, health and other organization identities), position level and permissions information, roles and access control lists (ACLS) and, additionally, different data compartments in their profile such as official identities, preferences for each organization, medical data, professional competences, etc.; the data of the individual is securely encrypted and stored locally in one or more electronic devices (mobile phone, smart watch, tablet, computer, . . . ) and self-managed by the individual or by one or more verified legal guardians, registered and associated with such individual in the system.

A cryptographic hash results from a mathematical function that maps data of an arbitrary size into a fixed sized string of bits, known as the hash value or simply the hash. The given input data always results in the same hash. Consequently, if a data does not match the hash value associated with it, the data has been tampered with.

To certify the identity of an individual in the system, it is required to do a verification of the individual's data by authorized personnel with permission to perform this task, such as (but not limited to) certified health professionals (medical professionals or veterinarians), verified public officials and security personnel (police, . . . ). Once the identity of the individual has been verified, for example by checking the authenticity of the nationality or citizenship data of the individual by authorized personnel by means of an official document, the verified data will be certified in the system and a hash value will be generated from this verified data. Then, this hash can be stored in the system and in one or more blockchain systems, wallets or other solutions, to certify the authenticity of the data and to ensure the immutability of the data in future verifications of the hash of the individual's identity.

For the data encryption, each registered individual or organization will have their own encryption, decryption and signing keys, securely stored for example in a permissioned blockchain solution. When an authorized individual/organization or a group of individuals/ organizations want access to some data of any individual, a request will be made to the system. If the source of the request doesn't have access rights for accessing the required data of such individual, the system will ask the individual or the designated legal guardians or approved contacts for emergencies to obtain that permission. Once the source of the request has obtained the access rights for the required data, the system generates a unique origin-destination relationship, preferably based on UUID/OID standards. In addition, encryption keys for such relationship will be generated for a secure private connection and/or encrypted data exchange. The entire process is recorded and audited, preferably in a blockchain solution, to ensure the authenticity and immutability of the data (audit of access logs and access permissions granted and revoked).

In this way, individuals control the information related to their person and to other individuals (minors, dependents, animals). By using the users devices to store their personal data and related individuals' data, and cloud and/or other mediums for data backup, the blockchain can act like a directory of pointers to an individual's data, stored in more traditional system and takes additional steps to implement the GDPR's "privacy by design and default" principles. Individuals give limited access to third parties, and provide only the information that is needed to transact the business at hand, and only for that specific purpose. Because the record of the access is recorded in the blockchain, just like the GDPR requirements, there would be an immutable record of who was accessing the information and how the information was being used.

Storing all personally identifiable information in separate "off-chain" databases (users' electronic devices, cloud services, . . . ), and only having references and other information along with a hash of this data in the blockchain, is one way to completely erase data in the off-chain database, in compliance with GRDP requirements. So, when someone exercises their "right to be forgotten," the personal data can be deleted, whereby the service provider erases the "linkability" of the blockchain hash pointer to the data located in distributed off-chain servers. This makes the referral information on the blockchain useless, without shattering the blockchain.

The use of pseudonymization techniques in combination with data stored off-chain (pseudonymization with pointers to personal data stored off-chain) is a manner which allows the personal data to be destroyed and thus removes the link to the data on the chain.

In this combined on-chain/off-chain setup, individuals control their data. The data that is registered on the blockchain (on-chain) facilitates aspects like non-repudiation, data integrity, distributed trust, etc. The data that is stored off-chain is verified against the data that is stored on the blockchain (such as hashes), before it is used. So, also in this hybrid case where the actual content is stored off-chain, the blockchain principles and advantages, such as decentralized trust, are still standing. The mobile device of the user acts as a secure server and will manage the secured encrypted data of one or more individuals associated with the user. The user can manage the access rights for different organizations and the type of information to be shared.

There are different types of data for sharing through the proposed unified identification protocol: public, private, emergencies and anonymised data. Public and anonymised data can be shared without encryption, for example, by NFC or QR code and using vCard standard format, also health data can be shared trough HL7 v2 and FHIR standard formats. Private and emergencies data are cypher texts. Emergencies data encryption is managed by the system and the system will provide the data approved by the user for this case to certified emergency services, using preferably a blockchain system for the storage of the encryption keys and for audit logs.

Private data encryption is self-managed by the user. The private data is encrypted in the user mobile and the user can share this data, for example, by generating a re-encryption key using asymmetric key encryption. The re-encryption key is generated by the user using the public keys provided by the approved recipients, and this re-encryption key is used to re-encrypt the cypher text of the user, which is transmitted and decrypted by each of the approved recipients through their own private key.

Additionally, user can approve some recipients to automatically access some data without continuously asking for the user approbation (the system acts as a re-encryption proxy). In this case the cypher text of the related individuals will be automatically synchronized with the system, which also will be able to access the re-encryption keys generated by the users for the approved recipients. The system translates cypher texts encrypted under user key into cypher texts encrypted under the recipients' keys. The system acts a re-encryption proxy and doesn't see the content of the messages being translated, nor can it re-encrypt user's messages to users for whom the user has not granted decryption rights.

For backup copies, the user may choose to save an encrypted copy in one or several online services (replication), download the information encrypted in a file, or divide the information and save the different parts in different locations, and each part may be also replicated in other locations. Optionally, the unified identification protocol also allows selecting contacts to save the different parts of the backup and their replications. The contacts will have to approve that these parts are saved in their device, but only the user will know in how many parts the information has been divided and how many times each part is replicated (preferences are stored in the user profile). In case of loss of data the user can recover the data from these distributed and replicated copies. Optionally, the user may also allow certain emergency contacts that the user has established to recover a backup of their data in the system in case of accident and destruction of the user's device, so that emergency and health services can access user health data in these situations (preferences for emergencies are stored in the system), being registered and audited each and every one of these operations in one or several distributed ledger technologies or blockchain.

JSON Web Token (JWT) is an open standard (RFC 7519) that defines a compact and self-contained way for securely transmitting information between parties as a JSON object. This information can be verified and trusted because it is digitally signed. They are useful for authorization and data exchange purposes. JWTs can be signed using a secret (with the HMAC algorithm) or a public/private key pair using RSA or ECDSA and consist of three parts: header, payload and signature. The signature certifies that only the party holding the private key is the one that signed it, to be sure the senders are who they say they are. Additionally, as the signature is calculated using the header and the payload also can be verified that the content hasn't been tampered with.

HTTP messages are simple, formatted blocks of data. Each message contains either a request from a client or a response from a server. They consist of three parts: a start line describing the message, a block of headers containing attributes, and an optional body containing data. Custom HTTP headers are commonly meant to provide additional information and even implementing particular logic on the server-side. For example, JWTs are exchanged in the header section of the HTTP message. The entity body or message body (or just plain "body") contains the message data. The body can contain text (e.g. JSON, BASE64) or binary data or can be empty.

Some situations may require the transfer of data between electronic devices, especially in situations or locations with little mobile network and/or Wifi connectivity or when the connection is not available (e.g., natural disasters). For this, the user's device can use, for example, NFC, Bluetooth, ad hoc mobile network (MANET) and even visual codes for data transmission (such as QR codes). In these situations, the first step is for the electronic device (s) requesting access to the information of an individual to present their credentials to the individual and their request for access to said data, for example by means of a QR code that is scanned by the individual and/or wireless transmission through NFC, Bluetooth and/or other alternatives.

It should be noted that both the application of the individual and the application of the organization and/or staff requesting access to information can have a memory cache that contains both information of organizations, people and devices to which they have authorized access to the data and also information received from the system to be able to validate the authenticity of the other party in off-line mode (without internet connection), for example by using JWTs, in such a way that the information stored in the cache of the application of the individual serves to verify by the individual that the origin of the request is a valid and safe origin and that it has been correctly authenticated in the system in a previous moment (when there was an internet connection).

The individual, after reading or receiving said request through the application in the mobile device, will be able to carry out the necessary verifications to check the received request, as, for example, to verify if the device or the organization/staff making the request is reliable and/or if they are previously authorized by the individual to access said data. Then, if the person approves the request, the data requested and additional information (for example, the keys for re-encryption or decryption) will be sent and/or will be shown to the source (s) of the request for processing, by using JWTs or other embodiments. Both the electronic device of the individual and that of the organizations and/or personnel that make the request for access to the data will store in the cache the entire process to subsequently synchronize the data in the system once the internet connection is restored (audit).

It should be noted that the user may associate different devices and applications to every individual registered in the system, provided that they have the necessary access rights (legal guardian, medical professional, etc.). Likewise, the devices and applications may request permission to access both the data of one or more individuals and to the profile associated to each individual registered in the system, in order to store their own data, generating the system in this case a profile for each device and/or application within the profile of each individual and associating, where appropriate, a unique and universal identifier for every associated device.

Additionally, the user may authorize the system to track the location of individuals for emergencies through geolocation devices, mobile telephony or other devices associated with these individuals. The devices or the individual's own application may exchange location data and other data in real time with the system for being used in case of an emergency and to prevent incidents. Likewise, the individual may have associated one or more individuals as contacts for emergencies.

The application of the individual or a device may issue the geolocation of the individual and, optionally, publish this information in the system, either anonymously or non-anonymously for certain contacts, organizations or personnel, in such a way that any individual can detect the presence of other (s) within a certain radius of action. For example, a cyclist and a pedestrian can have anonymous tracking enabled by geolocation and, thus, be able to visualize or warn of a possible collision between them through the application and/or device.

The application of the individual or a device may also detect a problem, emergency or accident. For example, a collision can be detected using an accelerometer and/ or other options. Similarly, a pet or a dependent person and their legal guardians can have activated tracking by non-anonymous geolocation, to detect a possible incidence through the application and/or the device such as the approach of the individual to a road, distancing from a place or of a certain distance range, etc.

In case of an accident or an emergency, either automatically by the application and/or device or manually by a specific button in the application or on the device, the unified identification protocol can send information to the emergency services and/or designated emergency contacts, by SMS or other embodiments, such as: the universal multi-purpose identifier, universal identifier of the device (s), geolocation of the individual or the last known (s), Wi-Fi or other detected nearby networks, as well as information of emergencies approved for the individual, among others.

On the other hand, the system can also cross environmental data, data collected from the devices and health data of the individual to propose activities or warn of certain circumstances. For example, the system can warn the individual and/or their legal guardians about levels of contamination, pollen or extreme maximum temperatures in areas or routes that the individual frequents, in order to avoid risks to their health.

Token is defined by The Oxford Dictionary as "a thing serving as a visible or tangible representation of a fact, quality, feeling, etc." and also "a voucher that can be exchanged for goods or services, typically one given as a gift or forming part of a promotional offer." Tokenization of services and use of tokens creates many opportunities for incentivizing, rewarding or even 'paying' users and healthcare ecosystem stakeholders to pursue beneficial activities. It can include token rewards for pursuing healthier lifestyle activities (i.e. better diet, more exercise, and fewer vices) or sharing healthcare data with the medical community and/or pharmaceutical companies. Gamification techniques have proven effective for specific healthcare applications, especially those focused on positive behavior modification, and can be the drivers that enable healthcare ecosystem players to achieve their goals faster and more uniformly.

While non-fungible digital assets were already possible on regular servers, they relied on centralized architecture and oversight—someone's server was in charge which meant they could disappear overnight, change some of the values on some of the assets, print new assets at will without anyone knowing, and more. Blockchain makes this transparent and immutable (unchangeable).

Computer system administrators commonly utilize event viewer consoles to perform system(s) monitoring tasks for viewing information, advertences and errors from applications and from the system running, in one or more computers, servers and/or devices. By utilizing this approach in healthcare, the described unified identification protocol can show, get from or send to other applications, organizations or systems the data and events of the individuals and of their devices, and make them available both to the individual and of their legal guardians and/or authorized personnel. In this way, the system can provide to authorized personnel health data, training data, identity data and other data from the individual, such as physical activity data, sleep cycle records, regular locations and/or and routes of the individual, related environmental information (pollution levels, pollen levels, . . . ), as well as other types of information. Likewise, the user may decide on the information to which their authorize the access and/or the transfer of data, as well as the type of data that is shared (public, anonymised and/or private data). The system allows classifying and selecting the type of information according to the origin (device, application or health profile of the individual) as well as depending on the type of event (informative, warning, risk, device errors . . . ). This allows a greater and better monitoring of the health of the individual and the search for common patterns in the appearance, treatment and solution of health problems in a group of individuals.

As an example, a patient in treatment who participates voluntarily in a education program, can be supervised by the teacher (health professional) in that training program and by one or several professionals (doctor, nurse, physiotherapist, psychologist, etc.) and jointly analyze the improvements that occur in the health of the individual according to their habits and other factors (diet, exercise, hours and quality of sleep, medications, etc.). In addition, the patient can share their anonymised data for research and, in this way, it will be able to compare their data with other participants in the training program or with other patients, thereby facilitating medical research. Additionally, individuals who participate in training courses can receive tokens for participating in these courses and to achieve certain objectives, to encourage the formation of individuals (gamification).

The unified identification protocol allows, using blockchain technology, a new level of security and the certification, notarization and auditable traceability of the information exchanged in a transaction, and the access to and independent and secure way to verify that the information joined to the transaction has not been tampered with, such as each access permission granted, medical or veterinary process registered, change of legal custody, individual-organization relationship established, data exchange and type of data sent/ received, reward/payment made, training acquired, degree obtained, professional competence acquired, official identity verified, among others. The immutability of blockchain ensures that the record of transactions made is untampered and secure. Information isn't stored on the blockchain, only the certification and audit trail.

Individuals and organizations can verify rewards and payments. Through blockchain solutions, individuals can simply use an app for authentication. The solution will store their encrypted identity, allowing them to share their data with organizations and manage it on their own terms.

In the above described unified identification protocol, the individuals are always the owner of their data and it can be synchronized with different organizations and authorized personnel such as healthcare professionals, public officials, and others. The individual is able to have their universal identity data and can decide which additional data they want to share and the format of this data (public, anonymised, private, emergencies) not only for digital transmission but to be stored in a QR code or in NFC trough an electronic device (mobile phone, smart watch, . . . ), plastic card, bracelet or other embodiments. Data can be stored in QR or NFC by using vCard custom fields or in other formats (FHIR, HL7 v2, LOINC, MSON . . . ) and can be exchanged in different formats too. The unified identification protocol adds Access Control Lists (ACLS) security and data hash at different data structure levels (field, form, access rights data and message levels). These goals are achieved, by the use of, but not limited to, custom HTTP headers for secure and unified data exchange among the different standards and formats.

It should be noted that this unified identification protocol utilizes customized fields in the different formats and standards that exist, as an expansion of the existing ones, for the transmission, certification and storage of information, in a unified manner among the different systems, formats, and standards available (vCard, FHIR, LOINC forms, HTTP headers, JWTs . . . ). As a non-limiting example, it will be used to designate these personalized fields the character "X" followed by a hyphen and then the characters "UHC" o similar, which are globally unused, and then another hyphen followed by the name of the field. The multipurpose identifier for the individual (X-UHC-MID) can be associated with other individuals (X-UHC-MID) and also with several multipurpose identifiers for relationships with entities, devices and others, based on UUID, OID, and/or DID formats, such as, in a non-limitative manner.

Personal Identifier (PID), which is stored as X-UHC-PID: unique and private personal identifier for every individual which is associated both with the individual's profile and with the X-UHC-MID. It can be different in each user device. Universal Identifier for Blood Donors and Other Types (UDR), which is stored and shared as X-UHC-UDR: unique identifier for donation purposes and proposed as universal health identifier. Health Identifiers (HIDs), which are referred as X-UHC-HID: different private identifiers from health centers, insurance companies, administrations, etc. Identity Identifiers (IIDs), which are referred as X-UHC-IID: different identifiers from public/private identity solutions and authentication services.

Entity Identifier (EID), which are referred as X-UHC-EID: unique identifier for every entity in the unified identification protocol. Listing Identifier for Professional Services (LID), which are referred as X-UHC-LID: unique and public professional identifier for an individual in a concrete entity or for concrete entity a service, which is used to be shown to the users and is associated to a X-UHC-EID or to a X-UHC-EID. Relationship Identifier (RID), which are referred as X-UHC-RID: unique and private relationship between an individual and an EID(s) and/or LID(s) and associated to them. Client Identifiers (CIDs), referred as X-UHC-CID: several client identifiers for different companies and services, associated to a X-UHC-MID. Executed Transaction Identifier (XID), which are referred as X-UHC-XID. Training Course Identifier (TID), this is referred as X-UHC-TID. It can be associated to X-UHC-EID, X-UHC-LID and X-UHC-MID.

Process/Product Identifier (PRD), which are referred as X-UHC-PRD. The processes can be associated with each other; a product is considered as the end of a process and is associated with it. Qualification Identifiers (QIDs), which are referred as X-UHC-QID, both for training qualifications as well as for virtual awards and other rewards obtained after some process completion, associated to a X-UHC-MID. Biometric Identifiers (BIDS), which are stored as X-UHC-BID plus a number for corresponding to each of the different Biometric Identifiers of the individual (e.g.: X-UHC-BID-1, X-UHC-BID-2), associated to X-UHC-PID and X-UHC-MID; Wallet Identifiers (WIDs): which are referred as X-UHC-WID plus a number, corresponding to each of the different Wallets of the individual (e.g.: X-UHC-WID-1, X-UHC-WID-2), associated to X-UHC-MID and X-UHC-PID; Device Identifier (DEV) which are referred as X-UHC-DEV. It can be associated to an individual's device or a medical/veterinary device, among others (company device, . . . ); Public Key (PK) and Private Key (SK), whose are generated from and associated to some of the above identifiers (for example: X-UHC-RID-PK and X-UHC-RID-SK). Access Control Lists (ACLS), which are referred as X-UHC-ACL and contains different roles and access permissions to different data fields, objects, profiles, etc. Encryption Information (ENC), which are referred as X-UHC-ENC and contains a list with data fields, objects, documents, profiles, etc. and information about the type of encryption applied (plain text, anonymised data, encrypted data, anonymised and encrypted data . . . ).

The unified unified identification protocol enables a computer implemented system described essentially comprises a method and the method comprises the following: Creation of a unique and non-transferable public multipurpose identifier (X-UHC-MID) and a personal identifier (X-UHC-PID) based on UUID, OID formats and/or others, associated to a profile for every individual and to additional public/private identifiers such as the universal donor identifier (X-UHC-UDR); Creation of a unique entity identifier (X-UHC-EID) for each entity associated to the unified identification protocol, based on OID or other formats; Creation of a unique listing identifier (X-UHC-LID) based on OID, DID or other formats, both to a specific service in an entity or to an individual which is a registered and certified professional and/or is an employee with some defined role; Creation of one or more relationship identifiers (X-UHC-RID) and the associated encryption keys, based on DID or other formats, for the different relationships between an individual and one or more entities (X-UHC-EID), services and/or professionals (X-UHC-LID), and update the individual's profile; Creation of one or more client, health, identity and/or wallet identifiers, among others, and update the individual's profile; Creation of, when required, Training Courses Identifiers (X-UHC-TID), Qualification Identifiers (X-UHC-QID), Transaction Identifiers (X-UHC-XID) and Process/Product Identifiers (X-UHC-PRD) such as enrollments, payments, competence levels, processes, health training courses for self-care, among others. Storage of the generated multipurpose identifiers in one or more cloud systems(s) and in one or more distributed ledger technologies, verifiable by the different individuals, entities and systems; Storage of the multipurpose identifiers related with the individual and of the data of the individual profile in one or several portable electronic devices of the individual and/or of the legal guardian(s) (mobile phone, smartwatch, tablet, bracelet, identity integrated circuit, . . . ), additionally in one or more cloud services(s) accessible by the different systems based on the user preferences and on other requirements (data structure and/or unified identification protocol requirements, data backup, emergency purposes, . . . ), and registering the transaction(s).

Certification of the data in the profile of the individual and of the access rights approved by the individual or by the legal guardian (s) in one or more distributed ledger technologies accessible by the different systems; Identification of the individual through the multipurpose identifier of the individual (MID), codified in QR, NFC or other realizations, carried out in an entity and/or by authorized personnel to access the data profile of the individual, verify if a previously created relationship exits and also if the necessary access rights to access the data required by the organization/professional exist, request access to the required data if the access rights do not exist or do not match those necessary to perform the data exchange, register the access grant when the permission is obtained, create a unique relationship if it does not exist and update the information in the individual's profile. Assigning access rights to the source(s) of the request of the required data of the individual's profile, carried out by the individual themselves, by the legal guardian(s) or by one or more designated emergency contacts, and send the required information in plain text (public data) or generate a re-encryption key by the system (emergency data) or by the individual or the legal guardian (private data) to be de-ciphered by the source(s) of the request, send the data requested and register the data exchange transaction. Send the data required by an entity from the servers of the cloud system(s) accessible by the different parties if the user has previously given authorization for permanent access to said data, without the need for repeated approval by the user (for example data for emergencies), and register the data exchange transaction. Certification in one or more distributed ledger technologies of transactions such as virtual awards and/or rewards, permissions granted, medical or veterinary processes registered, change of legal custody, relationships established with the individual, data exchanged and type of data sent/received, payments made, training and professional competence acquired, official identity verified, among others.

Optionally, the method also contemplates: Obtaining information automatically about entities (health and training centers, pharmacies,) and professionals (caregivers, trainers) to verify that they are legally registered and to avoid fakes. Obtaining results of the individuals from entities and professionals (attendance and connection of individuals to courses and education programs, level of satisfaction of the individuals, statistics, medical processes, training and competence data, official identity verified, . . . ), notify to the individual and/or to the legal guardian(s) if the profile must to be updated, send this data to the individual's related devices and, additionally, incorporate the data automatically into the profile of the individual in the system for emergencies, research purposes or for data backup, and store and certify the data in the cloud system(s) and distributed ledger technologies. Obtaining preferences, interests, individuals' location among other data, notify to the individual or to the legal guardian(s) relevant information related to the individual preferences or that adapt to the individual's profile and update the information in the system.

Associate wearable devices, health/sports devices and other sensors or devices to the individual's profile, creation of a relationship for each one, associate access rights for that relationship, storage the device data in the electronic device of the individual and/or in the cloud system(s), associate access rights both to each specific device and to the data related, automatic update of the individual's profile and automatic data exchange with the different relationships if approved by the user; Monitoring and tracking the individual through the unified identification protocol, if previously approved by the individual or by the legal guardian(s), to obtain geolocation data, sensors data and devices data of the individual and to alert if there is a danger, risk to health or other problems, and share that information, whether anonymously or non-anonymously, for certain contacts (legal guardian(s), contacts for emergencies), entities or personnel, in such a way that the authorized personnel can have access to said data. Automatic detection, through the unified identification protocol and the unified multipurpose identifier, of the existence of risks or their probability. For example, a collision can be detected by the use of accelerometers on the devices of one or more individuals. Similarly, the legal guardians of a minor can activate tracking by geolocation and detect a possible risk through the application and/or devices, such as the remoteness of the minor outside of a maximum allowed radius from the legal guardian(s) or the approach of the minor to an area of risk (roads, etc.).

Send information to the emergency services and/or designated emergency contacts, by SMS or other embodiments, in case of an accident or an emergency, carried out either automatically by the application and/or device or manually by a specific button in the application or on the device. The unified identification protocol can send information such as: identifiers of the individual (unified multipurpose identifier), universal identifier of the device (s), geolocation of the individual or the last known (s), WiFi or other detected nearby networks, as well as information of emergencies approved for the individual, among others. Obtaining cross environmental data, data collected from the devices and health data of the individual to propose activities or warn of certain circumstances. For example, the system can warn the individual, their legal guardians or the personnel about levels of contamination, pollen or extreme maximum temperatures in areas or routes that the individual frequents, in order to avoid adverse reactions.

The utilization of the unified identification protocol's system access to the unified identification protocol and the contained data will be done on a secure computing medium for the exchange and storage of data, using one or several of these options, without excluding other possible realizations: API, VPN, blockchain, Smart contracts, JWTs.

It should be noted that the multipurpose identifier of the individual is generated either by the individual himself through an electronic device with the software of the aforementioned application or by one of the registered and authorized entities and/or professionals, also through the application installed on some electronic device or computer.

The unified identification protocol can obtain information related to some multipurpose identifiers such as device data generated, results obtained (e.g.: attendance and connection of individuals to services or products such as self-care training programs, level of satisfaction), statistics, among others, and can send a notification to the required multipurpose identifiers when the data collected is available for consultation and for making the required actions (update, synchronize, smart-contract, . . . ).

Additionally, the data obtained can be exchanged with and between authorized multipurpose identifiers for healthcare monitoring and improvement, research studies, and optionally get virtual awards and rewards (tokens, payments, etc.); Also, can be obtained data from different multipurpose identifiers (cross environmental data, physical activity data, geolocation, health data of the individual) and notify proposed activities or warn of certain circumstances or their probability (levels of contamination, pollen levels, extreme maximum temperatures, risk zones, collision between individuals/devices, . . . ).

Optionally, the unified identification protocol allows acquire preferences, interests and locations to automatically detect the presence of available products and/or services (within a range of action), such as health services/training courses, and generate a notification to the multipurpose identifier(s) indicating products/services available in one or more territories and entities nearby and/or preferred by the individual(s).

The unified identification protocol also allows the certification in one or more distributed ledger technologies of the authenticity of the multipurpose identifiers of individuals, entities, services, processes and products, among others, carried out by registered and authorized authorities, entities and personnel; generate a multipurpose identifier for that transaction (X-UHC-XID) and notify the result of the transaction to the related multipurpose identifiers.

The conditions to carry out a transaction of information can be checked to verify valid or invalid credentials or access rights, missing data, uncertified parties, etc. and notify this information to the multipurpose identifiers. The identification multipurpose identifier generated for each individual also allows the content of the information it incorporates to be varied and, consequently, the automatic updating of the details of the individual's data and their profile accessible by the different systems.

The described procedure for the unified registry and universal identification of courses and individuals in patient and health training programs consists of an object of unknown characteristics thus far for the purpose of which it is intended, reasons which, combined with its practical utility, provide it with sufficient grounds to obtain the privilege of its exclusivity that is required.

Each of the steps described herein can be performed using a general purpose computing device, e.g., a personal computer, personal digital assistant, and/or computing device that is in communication with a network, e.g., internet, intranet, or extranet, that includes a memory and a set of instructions, that is, logic, specifically scripted to perform the functions, steps, communications, and data manipulations described herein. As the present invention is not limited to any specific instruction set, e.g., code, usable to implement one or more aspects of the present invention, and as those skilled in the art are well aware of the ways to instruct such a computing device to implement such functions, steps, communications, and data manipulations, further details of such specific instruction sets will not be provided here so as to not obscure the present invention. While one or more of the functions, steps, communications, and data manipulations can be performed by hand or by a computer-implemented instruction set, the present invention is not limited to any one sub combination thereof. Data gathering can be performed manually, in a semi-automated manner (e.g., given to a human person who then inputs the data into a computing device's memory), or in a fully-automated manner (e.g., the customer interacts directly with a computing device to input the data into a computer's memory). As will be readily appreciated by those skilled in the art, the present invention also includes the use of multiple computing devices on a communications network (including the use of removable memory media to transfer data between devices), including that the computing device via which data is input by any one human user is different from a computing device that implements decision instruction sets.

As mentioned, there remains the foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood, however, that even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

As the attributes of the presented invention have been sufficiently described, as well as how to put it into practice, it is not considered necessary to make a more extensive explanation so that any expert in the matter understands its scope and the advantages that derive from it, clarifying that, within its essence, it may be put into practice in other ways of implementation that differ in detail from the application thereof indicated by way of example, and which will also reach the protection that is sought, provided that it is not altered, changed or modified in its fundamental principle.

What is claimed is:

1. A computer implemented system to unify and certify a data and an identifier using a unified identification protocol in at least two operational phase, the computer implemented system comprising: an online electronic network device, the online electronic network device comprises:
    a display;
    a computer-readable memory;
    a computer processor coupled to the computer-readable memory programmed with executable instructions to configure the processor for processing a collection of software components; and
    a collection of software components stored in the computer-readable memory on a single platform, the software components being executable by the computer processor to:
    generate a group of multipurpose identifiers;
    generate a unique profile;
    generate at least one or more encryption keys;
    generate a hash value;
    identify a unique profile for each individual and associating with a group of identifiers;
    create a unique user profile associated to at least one personal identifiers in one or several user devices;
    generate at least one encryption key to each of the individual and to different relationship and set of multipurpose identifiers;
    identify the unique profile encoded in QR, NFC or other realizations carried out by an entity, a service or an authorized personnel through a software application and to request access to an information associated with the group of identifiers for creation of relationship with the encryption keys after receiving a request approval, if no previous relationship and access rights were established between the different parties;
    generate, register and automatically communicate an incident in case of existence of any impediment when making the identification, creating the relationship, accessing the data, making requests or exchanging data, and notify to the related multipurpose identifiers;
    store and update the information associated with the group of identifiers in a cloud system, in one or several portable electronic devices of the individual and of the legal guardian(s) and in a distributed ledger accessible by a set of different parties based on the access permissions obtained and then notify to the related identifiers for making a group of required actions and registering a transaction.

2. The computer implemented system as claimed in claim 1, wherein the multipurpose identifiers are unique, non-transferable and univocally distinguishable through the unified identification protocol for a group selected from a service, a process, a product, a qualification, a device, among others, such as an entity Identifiers, a listing Identifiers for professional services, a training courses identifiers, a process/product Identifiers, a qualification identifiers and a device Identifiers, carried out by an authorized and registered entities and a personnel.

3. The computer implemented system as claimed in claim 1, wherein the unique identification creates the multipurpose identifiers, unique, non-transferable and univocally distinguishable such as individual identifiers, personal identifiers, health Identifiers, identity identifiers, entity identifiers, listing identifiers for professional services, relationship identifiers, client Identifiers, executed transaction identifiers, training course identifiers, process/product identifiers, qualification identifiers, biometric identifiers, wallet identifiers, device identifiers, among others, by means of a set of alphanumeric characters defined by alphanumeric-hexadecimal translation maps that avoid confusion among them by a bad reading, based both on UUID, OID, DID formats and others, codified in QR, NFC, and other formats including additional information, and which are available for automatic reading by electronic devices and for human reading.

4. The computer implemented system as claimed in claim 1, wherein the set of information can be exchanged off-line in situations or locations with little mobile network or WiFi connectivity or when the connection is not available, using NFC, Bluetooth, ad hoc mobile network and even visual codes for data transmission, by means of maintaing a memory cache both the application of the individual and the organization or staff requesting access to information, these memory caches containing both information of organizations, people and devices to which they have authorized access to the data and also information received from the system to be able to validate the authenticity of the other party in off-line mode.

5. The computer implemented system as claimed in claim 1, wherein the user profile, the individuals' profiles, the different compartments and the data objects contained can be securely backed up, splitted and replicated in one or several online services or in one or more electronic devices of the user or of some selected contacts, so that backup can be combined and the data recovered from these splitted, distributed and replicated encrypted backup copies, in case of data loss and broken device.

6. The computer implemented system as claimed in claim 1, wherein a wearable devices, health/sports devices and other sensors or devices is associated to the individual's profile, creation of a relationship for each one, associate access rights for that relationship, storage the device data in the electronic device of the individual or in the cloud system(s), associate access rights both to each specific device and to the data related, automatic update of the individual's profile and automatic data exchange with the different relationships if approved by the user.

7. The computer implemented system as claimed in claim 1, wherein the application of the individual or a device issue the geolocation of the individual and, optionally, publish this information in the system, either anonymously or non-anonymously for certain contacts, organizations or personnel, in such a way that any individual detect the presence of other(s) within a certain radius of action and the application of the individual or a device may detect a problem, emergency or accident automatically or manually by a specific button in the application or on the device, and the unified identification protocol send an information to the emergency services and/or designated emergency contacts, by SMS or other embodiments, including the individual multipurpose identifier, device(s) multipurpose identifier(s), application or device's data, geolocation of the individual or the last known(s), WiFi or other detected nearby networks, as well as information for emergencies approved by the individual, among others.

8. The computer implemented system as claimed in claim 1, wherein the unified identification protocol allows to share data from different sources related to the same individual, to have the data unified in the individual's profile in a universal manner, to verify the authenticity of the information related to a same individual and also to know the authenticity of registered professionals and their qualification.

9. The computer implemented system as claimed in claim 1, wherein the unified identification protocol allows to have different payments modes associated with an individual, entity or established relationships, and the multipurpose identifier can be used to make payments manually or automatically.

10. The computer implemented system as claimed in claim 1, wherein authorized personnel monitor the data shared from the individual's multipurpose identifier through the established relationship by the different data compartments and devices associated with the individual's multipurpose identifier and approved in the relationship's access rights, so that the authorized personnel can view past data and real time data from the different devices and can make suggestions or diagnoses to improve the health of the individual.

11. The computer implemented system as claimed in claim 1, wherein the individual or their legal guardian can establish a relationship to share certain data for research purposes from their multipurpose identifier, associated to each of the individual's profile and the devices, through anonymised data exchange.

12. The computer implemented system as claimed in claim 1, wherein some required data by an entity is sent from the servers of the cloud system(s) accessible by the different parties if the user has previously given authorization for permanent access to said data, without the need for repeated approval by the user.

13. The computer implemented system as claimed in claim 1, wherein when a package of services or products are contracted by the users, they verify the authenticity of the whole pack and of all of its parts, such as verifying the authenticity of drugs and of the registered pharmacy when buying prescribed medication, as well as verifying the authenticity of a medical tourism pack and its components such as the agency, flight, hotel, medical center, registered practitioner(s), professional qualification and products/devices being used in the procedure, among others.

14. The computer implemented system as claimed in claim 1, wherein the unified identification protocol comprises:
   an information related to some multipurpose identifiers such as device data generated, results obtained statistics, among others;
   a notification to the required multipurpose identifiers when the data collected is available for consultation and for making the required actions;
   data from different multipurpose identifiers and notify proposed activities or warn of certain circumstances or their probability including levels of contamination, pollen levels, extreme maximum temperatures, risk zones, collision between individuals/devices; and
   data exchange and obtained with and between authorized multipurpose identifiers.

15. The computer implemented system as claimed in claim 1, wherein the unified identification protocol also comprises:
   preferences, interests and locations to automatically detect the presence of available products or services, such as health services/training courses;
   a notification to the multipurpose identifier(s) indicating products/services available in one or more territories and entities nearby or preferred by an individual.

16. The computer implemented system as claimed in claim 1, wherein the unified identification protocol comprises:
   certification in one or more distributed ledger technologies of the authenticity of the multipurpose identifiers of individuals, entities, services, processes and products, among others, carried out by registered and authorized authorities, entities and personnel; generate a multipurpose identifier for that transaction and notify the result of the transaction to the related multipurpose identifiers; the conditions checked to carry out a transaction are met by the different multipurpose identifiers, update the information related to the transaction request, and notify this information to the multipurpose identifiers.

17. The computer implemented system as claimed in claim 1, wherein the product or device identifier is associated with one or more identifiers of the product/device or of some of its parts, including a chemical composition or a cellular production line identification; a processor, a memory, a software or a network card identification.

18. The computer implemented system as claimed in claim 1, a specific object in the unified identification protocol is associated with at least one multipurpose identifiers for verification of a set of different information.

19. The computer implemented system as claimed in claim 1, wherein the set of different information includes a verifiable information of a client, a verifiable information of achieved goals and training and awards/rewards associated, verifiable claims for data as provider or a legal and administrative verifiable information, among others.

* * * * *